United States Patent
Ou Yang et al.

(10) Patent No.: US 10,207,033 B2
(45) Date of Patent: Feb. 19, 2019

(54) SENSOR-CONTROLLED NASAL ASPIRATOR

(71) Applicant: AVITA CORPORATION, New Taipei (TW)

(72) Inventors: Hsing Ou Yang, New Taipei (TW); Hsuan Hao Shih, New Taipei (TW); Ta Chieh Yang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 0 days.

(21) Appl. No.: 15/448,630

(22) Filed: Mar. 3, 2017

(65) Prior Publication Data

US 2017/0252495 A1    Sep. 7, 2017

(30) Foreign Application Priority Data

Mar. 4, 2016    (TW) .............................. 105203034 U

(51) Int. Cl.
*A61M 1/00* (2006.01)
*H04L 29/08* (2006.01)

(52) U.S. Cl.
CPC ........ *A61M 1/0066* (2013.01); *A61M 1/0003* (2013.01); *A61M 1/008* (2013.01); *A61M 1/0031* (2013.01); *A61M 2205/3306* (2013.01); *A61M 2205/3331* (2013.01); *A61M 2205/502* (2013.01); *A61M 2205/82* (2013.01); *A61M 2210/0618* (2013.01); *H04L 67/12* (2013.01)

(58) Field of Classification Search
CPC .. A61M 1/0066; A61M 1/0003; A61M 1/008; A61M 2205/3306; A61M 2205/3331; A61M 2205/502; A61M 2205/82; A61M 2210/0618

USPC .................... 604/73, 131, 65–67; 128/12, 13
See application file for complete search history.

(56) References Cited

U.S. PATENT DOCUMENTS

| 6,547,756 B1 * | 4/2003 | Greter | A61M 1/06 604/346 |
|---|---|---|---|
| 7,169,116 B2 | 1/2007 | Day et al. | |
| 9,492,068 B2 * | 11/2016 | Papania | A61M 11/005 |
| 9,827,355 B2 * | 11/2017 | Baker | A61M 1/0062 |
| 2009/0000024 A1 * | 1/2009 | Louis | E03C 1/046 4/676 |

FOREIGN PATENT DOCUMENTS

TW            528752        9/2016

* cited by examiner

*Primary Examiner* — Manuel Mendez
(74) *Attorney, Agent, or Firm* — Raymond Y. Chan; David and Raymond Patent Firm

(57) ABSTRACT

The present disclosure illustrates a sensor-controlled nasal aspirator including a distance sensing unit, a micro processing unit and an air pump. The distance sensing unit is configured to sense a distance between a target object and the distance sensing unit. The micro processing unit is configured to store a preset distance, and receive and process the distance transmitted from the distance sensing unit, and transmit an action command signal when the distance is not higher than the preset distance. The air pump is configured to receive the action command signal and performs a target action according to the action command signal.

7 Claims, 5 Drawing Sheets

SENSOR-CONTROLLED NASAL ASPIRATOR

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present disclosure relates to a nasal aspirator, and more particularly to a sensor-controlled nasal aspirator.

Description of Related Arts

For infants, young children or patients who are unable to take care of themselves and blow nose, nasal mucus may be stuck in nasal cavity and cause problem in breathing difficulty. Therefore, a device capable of sucking nasal mucus is developed to solve the problem. The conventional nasal aspirator has been developed from the manual nasal aspirator to the electronic nasal aspirator, and the developers make efforts to continuously and quickly clean the nasal mucus in nasal cavity.

Please refer to FIG. 1, which is a schematic view of a conventional nasal aspirator 1A. The nasal aspirator 1A mainly includes a suction head 2A and a switch button 3. In order to operate the nasal aspirator 1A to clean a user's nasal cavity N, the suction head 2A is inserted into the nasal cavity N first and then the switch button 3 disposed on a shell member of a handle is pressed to start cleaning.

However, the switch button 3 is disposed on the shell member, so the user may spend more time to find the switch button 3 by touch while operating the nasal aspirator 1A to clean nasal cavity N, and it causes that the user may miss the timing of pressing the switch button 3. Furthermore, after the user aligns the nasal aspirator 1A with the nasal cavity N, pressing the button 3 by the user's finger may shake the suction head 2A to deviate from the nasal cavity N. Moreover, after completing the operation of the nasal aspirator 1A, the user has to press the switch button 3 again to stop the operation, and it is inconvenient for the user. Therefore, what is need is to develop a nasal aspirator which may be operated more easily, stably and quickly.

SUMMARY OF THE PRESENT INVENTION

An objective of the present disclosure is to provide a sensor-controlled nasal aspirator which performs action according to a sensed distance of a target object, so that the nasal aspirator can be automatically driven to suck nasal mucus while getting close to the nasal cavity within a predetermined distance, thereby preventing from operational error.

To achieve the foregoing objective, the present disclosure provides a sensor-controlled nasal aspirator which includes a distance sensing unit, a micro processing unit and an air pump. The distance sensing unit is configured to sense a distance between a target object and the distance sensing unit. The micro processing unit is configured to store a preset distance, receive and process the distance transmitted from the distance sensing unit, and transmit an action command signal when the distance is not higher than the preset distance. The air pump is configured to receive the action command signal, and perform a target action according to the action command signal.

Preferably, the sensor-controlled nasal aspirator of the present disclosure further includes a switch unit configured to control power activation of the sensor-controlled nasal aspirator.

Preferably, the switch unit is a button switch.

Preferably, the distance sensing unit is an infra-red sensor or an ultrasound sensor.

Preferably, the sensor-controlled nasal aspirator of the present disclosure further includes a display unit configured to display indicators for remained power and suction strength of the sensor-controlled nasal aspirator.

Preferably, after the air pump completes the target action and the micro processing unit receives the distance, the micro processing unit transmits a stop command signal to the air pump for stopping the target action when the distance is higher than the preset distance.

Preferably, the micro processing unit stores a preset distance range, and determines whether an absolute value of a difference between the distance and the preset distance is out of the preset distance range, and according a determination result, the micro processing unit enables the distance sensing unit to resume sensing the distance or transmits the action command signal to the air pump to perform the target action.

The sensor-controlled nasal aspirator of the present disclosure can sense the distance of the target object and start target action (such as air extraction) when the sensed distance reaches to the preset distance, so that the nasal aspirator can be operated automatically within the predetermined distance. Therefore, the user can operate the nasal aspirator more quickly, accurately and easily, thereby reducing uncertainty and error in operation.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

Figure 1:
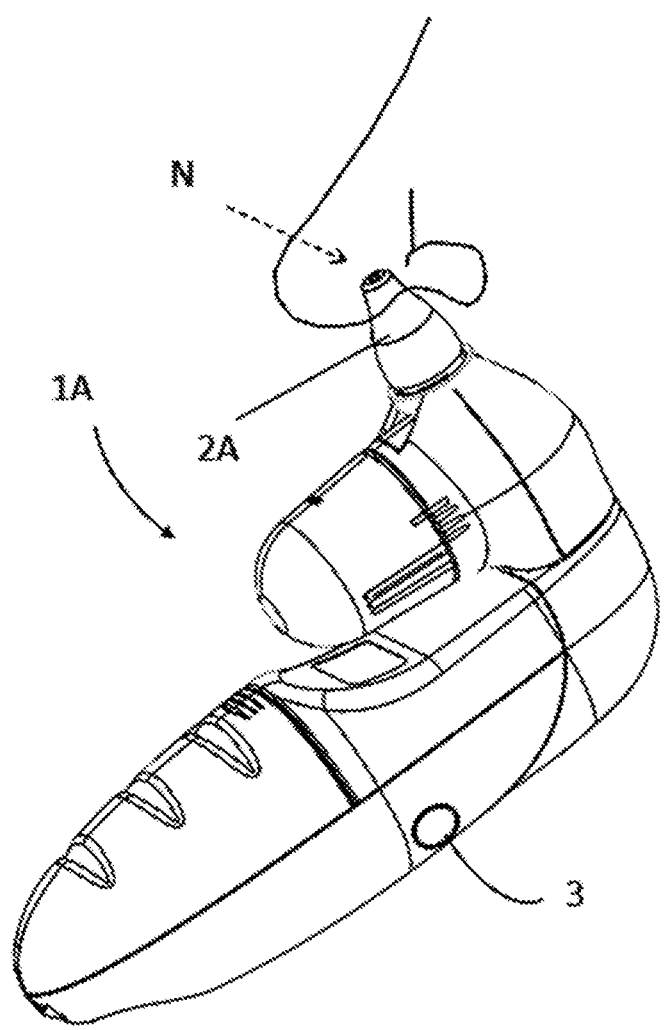
FIG. 1 is a schematic view showing operation of a conventional nasal aspirator.

The following embodiments of the present invention are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present invention. As used herein, the term "or" includes any and all combinations of one or more of the associated listed items.

Figure 2:
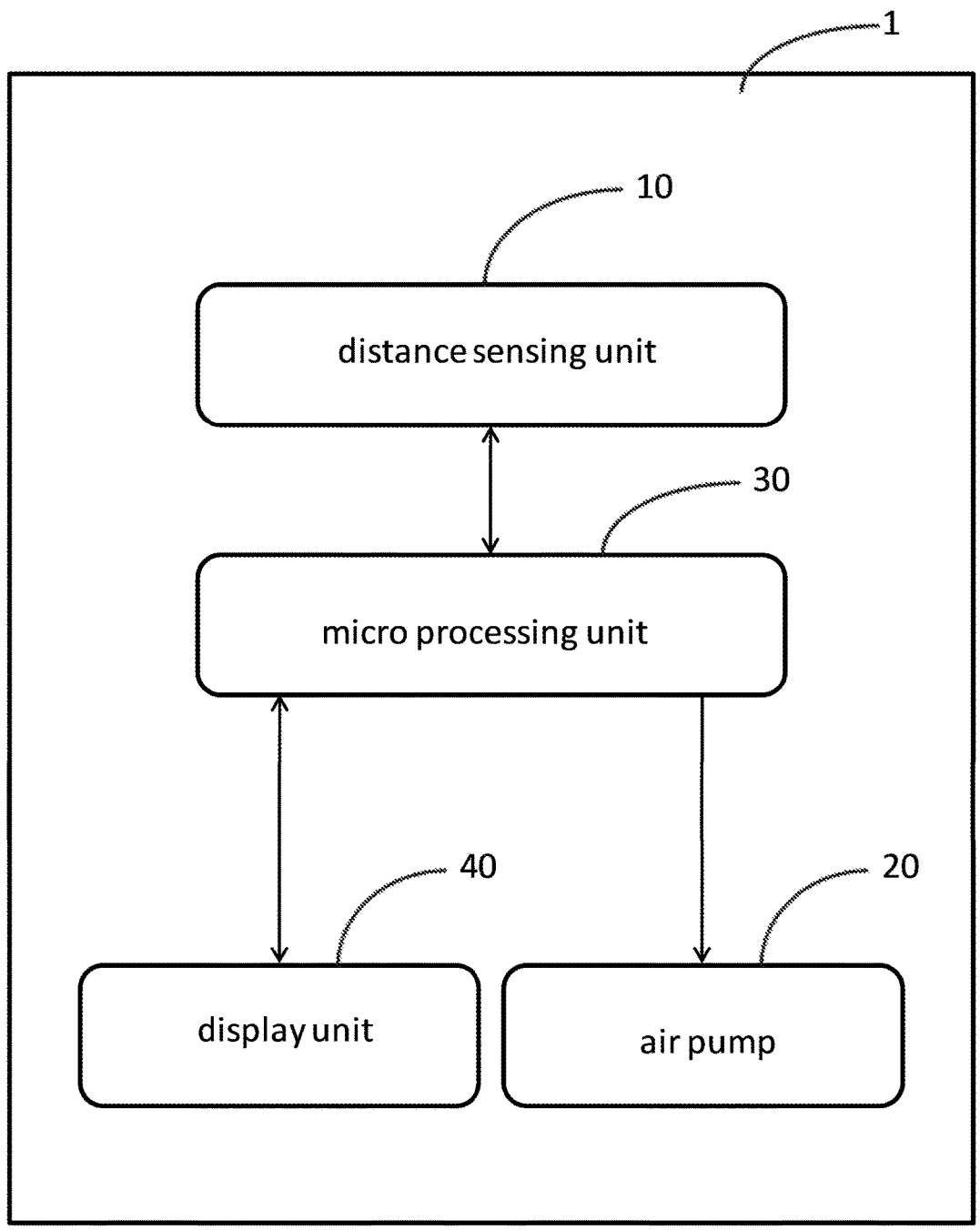
FIG. 2 is a block diagram of a sensor-controlled nasal aspirator of the present disclosure.
Figure 3:
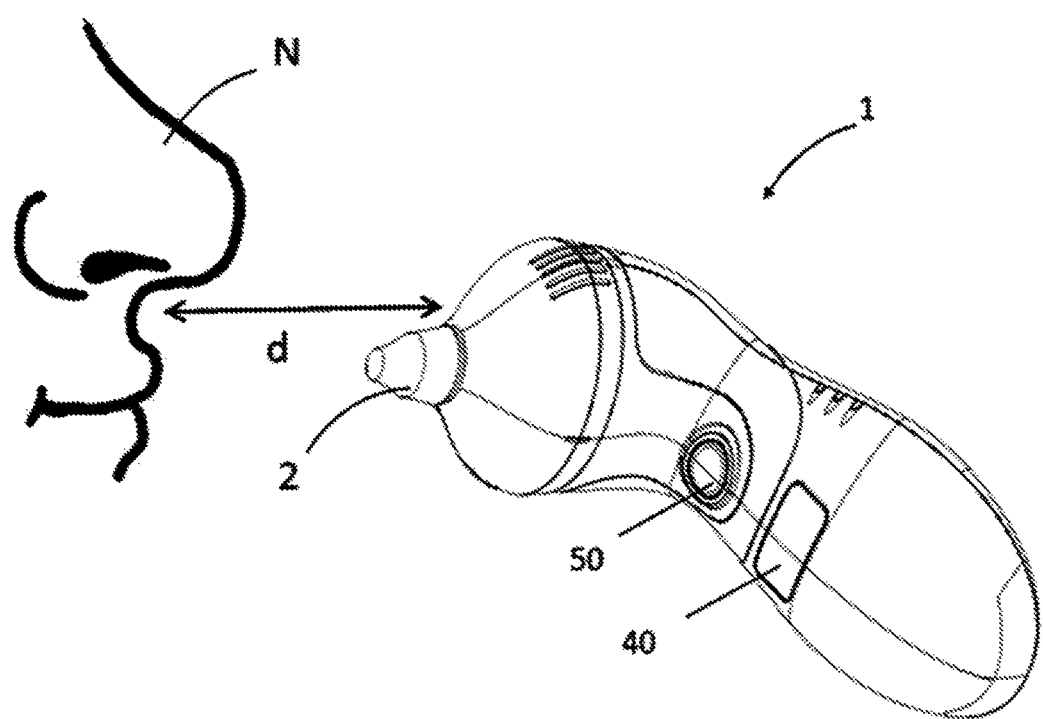
FIG. 3 is a schematic view showing operation of the sensor-controlled nasal aspirator of the present disclosure.

Please refer to FIGS. 2 and 3, which respectively show a block diagram of a sensor-controlled nasal aspirator 1 and a schematic view of usage of the sensor-controlled nasal aspirator 1, in accordance with the present disclosure. As shown in FIG. 2, the sensor-controlled nasal aspirator 1 includes a distance sensing unit 10, a micro processing unit 30, an air pump 20, a display unit 40, and a switch unit 50. The distance sensing unit 10 is configured to sense a distance between the distance sensing unit and a target object.

A micro processing unit 30 configured to store a preset distance d, receive and process a signal indicative of the distance transmitted from the distance sensing unit 10. The micro processing unit 30 transmits an action command signal when the distance is not larger than the preset distance d, as shown in FIG. 3. The air pump 20 is configured to receive the action command signal and then perform a target action according to the action command signal. The display unit 40 is configured to display indicators for suction strength and remained power of the sensor-controlled nasal aspirator 1.

The switch unit 50 is configured to control power activation of the sensor-controlled nasal aspirator 1, as shown in FIG. 3. Preferably, the switch unit 50 may be a button switch.

In this embodiment, the distance sensing unit 10 may be an infra-red sensor or an ultrasound sensor for sensing the distance.

Please refer to FIG. 3, which shows a schematic view of operation of the sensor-controlled nasal aspirator 1. In order to use the sensor-controlled nasal aspirator 1, a suction head 2 of the sensor-controlled nasal aspirator 1 is aligned with a target object, for example, the target object is a user's nasal cavity N. Next, the sensor-controlled nasal aspirator 1 is moved toward the nasal cavity N and the distance sensing unit 10 continuously senses the distance between the nasal cavity N and the distance sensing unit 10 until the sensed distance reaches to the preset distance d, and the micro processing unit 30 then transmits the action command signal to the air pump 20. Upon receipt of the action command signal, the air pump 20 performs the target action according to the action command signal. The target action may be an air extracting action to suck nasal mucus through the suction head 2.

Figure 4:
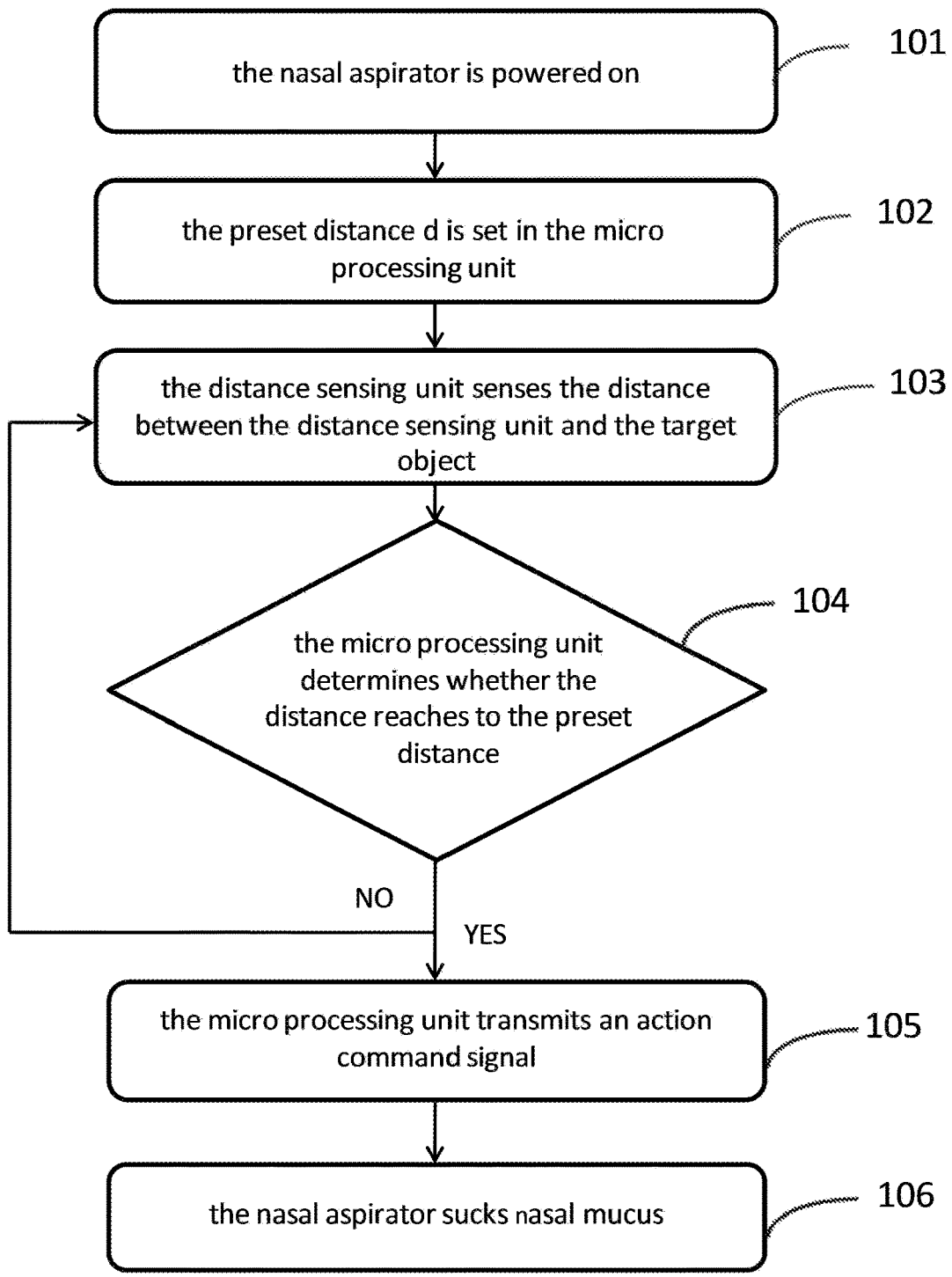
FIG. 4 is a flowchart showing the steps in an operation of the sensor-controlled nasal aspirator of the present disclosure.

Please refer to FIG. 4, which is a flowchart showing the steps in an operation of the sensor-controlled nasal aspirator 1 of the present disclosure. As shown in FIG. 4, in a step 101, the sensor-controlled nasal aspirator 1 is powered on. In a step 102, the preset distance d is set in the micro processing unit 30 in advance. In a step 103, the distance sensing unit 10 senses the distance between the distance sensing unit 10 and the target object, and transmits the sensed distance to the micro processing unit 30. In step 104, the micro processing unit 30 receives the distance transmitted from the distance sensing unit 10, and then determines whether the distance sensed by the distance sensing unit 10 reaches to the preset distance d, and a step 105 is performed if the sensed distance reaches to the preset distance d; and the step 103 is repeated to sense the distance if the sensed distance does not reach to the preset distance d. In the step 105, the micro processing unit 30 transmits the action command signal to the air pump 20. In a step 106, the air pump 20 is activated to extract air from the target object, thereby sucking nasal mucus from the nasal cavity N for cleaning purpose, for example.

Figure 5:
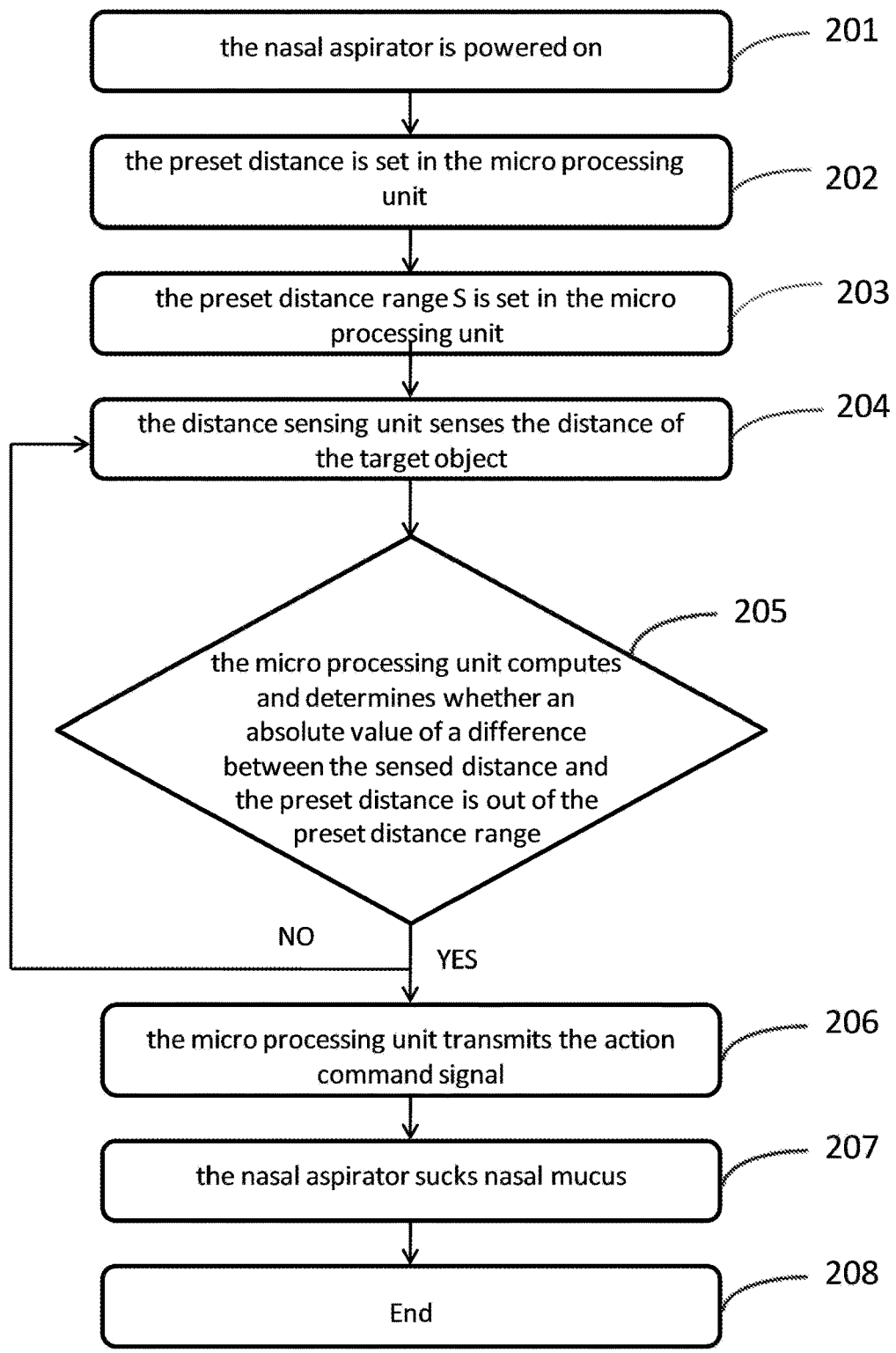
FIG. 5 is a flowchart showing the steps in an operation of other embodiment of the sensor-controlled nasal aspirator of the present disclosure.

Please refer to FIG. 5, which shows a flowchart showing the steps in an operation of other embodiment of the sensor-controlled nasal aspirator 1 of the present disclosure. As shown in FIG. 5, in a step 201, the sensor-controlled nasal aspirator 1 is powered on; in a step 202, the preset distance d is set in the micro processing unit 30 in advance; in step 203, a preset distance range S is set in the micro processing unit 30; in a step 204, the distance sensing unit 10 senses the distance between the distance sensing unit 10 and the target object, and then transmits the sensed distance to the micro processing unit 30; in a step 205, after receiving the distance sensed by the distance sensing unit 10, the micro processing unit 30 computes and determines whether an absolute value of a difference between the sensed distance and the preset distance d is out of the preset distance range S, and a step 206 will be performed if the absolute value is out of the preset distance range S. In the step 206, the micro processing unit 30 transmits the action command signal; if the absolute value is within the preset distance range S, the step 204 is repeated to continuously sense and obtain the distance. In the step 206, the micro processing unit 30 transmits the signal to the air pump 20. In a step 207, the air pump 20 is activated to perform the target action, that is, the air pump 20 extracts air to suck nasal mucus from the target object through the suction head 2 for cleaning purpose. In a step 208, the air pump 20 is turned off to stop sucking.

Furthermore, in this embodiment, after the air pump 20 completes the target action and the micro processing unit 30 determines that the sensed distance is higher than the preset distance d or the difference between sensed distance and the preset distance is out of the preset distance range S, the micro processing unit 30 transmits a stop command signal to the air pump 20 to stop the target action.

By using the sensor-controlled nasal aspirator of the present disclosure, the user can operate the nasal aspirator faster and more accurately, thereby improving convenience in operation and reducing uncertainty and error in operation.

The present disclosure disclosed herein has been described by means of specific embodiments. However, numerous modifications, variations and enhancements can be made thereto by those skilled in the art without departing from the spirit and scope of the invention set forth in the claims.

What is claimed is:

1. A sensor-controlled nasal aspirator, comprising:
a suction head arranged for aligning with a target object
a distance sensing unit for continuously sensing a distance between the target object and the distance sensing unit;
a micro processing unit operatively linked to the distance sensing unit to store a preset distance, receive and process the distance transmitted from the distance sensing unit, wherein the micro processing unit transmits an action command signal when the distance is not larger than the preset distance; and an air pump operatively linked to the micro processing unit, wherein the air pump is activated for extracting air at the suction head to the target object when the air pump receives the action command signal from the micro processing unit.

2. The sensor-controlled nasal aspirator according to claim 1, further comprising a switch unit being actuated to control the micro processing unit in an on-and-off manner.

3. The sensor-controlled nasal aspirator according to claim 2, wherein the switch unit is a button switch.

4. The sensor-controlled nasal aspirator according to claim 1, wherein the distance sensing unit is an infra-red sensor or an ultrasound sensor.

5. The sensor-controlled nasal aspirator according to claim 1, further comprising a display unit operatively linked to the micro processing unit, wherein the display unit displays indicators for remained power and suction strength of the sensor-controlled nasal aspirator.

6. The sensor-controlled nasal aspirator according to claim 1, wherein the micro processing unit transmits a stop command signal to the air pump to deactivate the air pump when the distance is larger than the preset distance so as to stop extracting air at the suction head to the target object.

7. The sensor-controlled nasal aspirator according to claim 1, wherein the micro processing unit stores a preset distance range, and determines whether an absolute value of a difference between the distance and the preset distance is out of the preset distance range; and wherein according a determination result, the micro processing unit enables the distance sensing unit to resume sensing the distance or transmits the action command signal to the air pump to perform the target action.

* * * * *